(12) United States Patent
Wiemker et al.

(10) Patent No.: US 10,332,238 B2
(45) Date of Patent: Jun. 25, 2019

(54) VISUAL ANONYMIZATION OF MEDICAL DATASETS AGAINST 3D VOLUME RENDERING

(71) Applicant: KONINKLIJKE PHILIPS N.V., Eindhoven (NL)

(72) Inventors: Rafael Wiemker, Kisdorf (DE); Thomas Buelow, Grosshansdorf (DE); Tobias Klinder, Uelzen (DE); Martin Bergtholdt, Hamburg (DE); Irina Waechter-Stehle, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 181 days.

(21) Appl. No.: 15/315,402

(22) PCT Filed: Jun. 22, 2015

(86) PCT No.: PCT/EP2015/063952
§ 371 (c)(1),
(2) Date: Dec. 1, 2016

(87) PCT Pub. No.: WO2015/197541
PCT Pub. Date: Dec. 30, 2015

(65) Prior Publication Data
US 2017/0200256 A1 Jul. 13, 2017

(30) Foreign Application Priority Data
Jun. 24, 2014 (EP) .................................. 14173573

(51) Int. Cl.
*G06K 9/00* (2006.01)
*G06T 3/00* (2006.01)
(Continued)

(52) U.S. Cl.
CPC .......... *G06T 3/0093* (2013.01); *G06F 19/321* (2013.01); *G06T 7/11* (2017.01);
(Continued)

(58) Field of Classification Search
CPC ....... G06T 3/0093; G06T 7/194; G06T 15/08; G06T 19/00; G06T 19/20
(Continued)

(56) References Cited

U.S. PATENT DOCUMENTS

| 5,859,928 A | 1/1999 | Noh |
| 8,867,812 B2 | 10/2014 | Brentwood et al. |

(Continued)

FOREIGN PATENT DOCUMENTS

| JP | 2007243256 A | 9/2007 |
| JP | 2008118406 A | 5/2008 |
| JP | 2013138800 A | 7/2013 |

OTHER PUBLICATIONS

Hu, J., et al., "A pixel-based scrambling scheme for digital medical images protection", Journal of Network and Computer Applications, Academic Press, NY, vol. 32, No. 4, 2009, Abstract.
(Continued)

*Primary Examiner* — Van D Huynh (57) ABSTRACT

Image processing method or apparatus (IP) to transform a 3D image data set (DS) into a visually protected one (DSX). The 3D image set includes an object region (OR) and a background region (BR) that defines s silhouette of an imaged object (P). An inadvertent or malicious direct volume rendering of the silhouette (IF) of the object is prevented by applying a randomization operation to at least the background region (BR).

20 Claims, 4 Drawing Sheets

(51) Int. Cl.
  *G06T 15/08* (2011.01)
  *G06T 19/00* (2011.01)
  *G06T 7/11* (2017.01)
  *G06T 7/194* (2017.01)
  *G06F 19/00* (2018.01)
  *G06T 19/20* (2011.01)

(52) U.S. Cl.
  CPC .............. *G06T 7/194* (2017.01); *G06T 15/08* (2013.01); *G06T 19/00* (2013.01); *G06T 19/20* (2013.01); *G06T 2207/10081* (2013.01); *G06T 2210/41* (2013.01)

(58) Field of Classification Search
  USPC ........................................................ 382/131
  See application file for complete search history.

(56) References Cited

U.S. PATENT DOCUMENTS

| | | | |
|---|---|---|---|
| 2004/0174998 A1 | 9/2004 | Youatt et al. | |
| 2008/0212742 A1* | 9/2008 | Hughes | G01T 1/167 378/98.12 |
| 2011/0311042 A1 | 12/2011 | Cheddad et al. | |
| 2013/0208966 A1* | 8/2013 | Zhao | G06F 9/5072 382/131 |
| 2013/0283061 A1* | 10/2013 | Jeong | G06F 21/602 713/189 |
| 2014/0214683 A1* | 7/2014 | Dominick | G16H 10/60 705/51 |
| 2014/0368526 A1* | 12/2014 | Day | G06T 11/001 345/589 |
| 2016/0048944 A1* | 2/2016 | Ashmole | A61B 6/032 382/131 |

OTHER PUBLICATIONS

Huang, H-C, et al., "Integrity preservation and privacy protection for medical images with histogram=based reversible data hiding", Life Science Systems and Applicaitons Workshop, IEEE, 2011, Abstract.

Zhou, Y., et al., "Selective Object Encryption for Privacy Protection", Proceedings of SPIE, vol. 7351, 2009, Abstract.

Suzuki, H., et al., "Anonymization server system for DICOM images", Proceedings of SPIE, vol. 6516, 2007, Abstract.

Magee, D., et al., "An augmented reality simulator for ultrasound guided needle placement training", Medical & Biological Engineering & Computing 45(10):957-967, Oct. 2007.

Laws, J., et al., "Feature hiding in 3D human body scans", Information Visualization (2006), 5, 271-278.

* cited by examiner

VISUAL ANONYMIZATION OF MEDICAL DATASETS AGAINST 3D VOLUME RENDERING

CROSS-REFERENCE TO PRIOR APPLICATIONS

This application is the U.S. National Phase application under 35 U.S.C. § 371 of International Application No. PCT/EP2015/063952, filed on Jun. 22, 2015, which claims the benefit of European Patent Application No. 14173573.8, filed on Jun. 24, 2014. These applications are hereby incorporated by reference herein.

FIELD OF THE INVENTION

The invention relates to image processing methods, to image processors, to computer program products and computer readable media.

BACKGROUND OF THE INVENTION

In the medical field, patient consent for having their X-ray or MR image taken for diagnosis or for making their imagery available for clinical studies is becoming an increasingly sensitive issue. This is even the more so, as medical image data becomes easily accessible through data networks. Also, it is now increasingly common to hand out the image data to patients on mobile storage devices such as CDs or memory sticks. Again this may invite for possible abuse or at least unintended misuse for at least the following reasons.

These days, many standard viewing software modules furnish the option for interactively controlled direct volume rendering (DVR). With DVR one can effect with ease displaying of volumetric renderings directly from 3D raster scan data without requiring a prior segmentation of the body or the organs.

But these 3D direct volume rendering options can be used to (possibly inadvertently or with malicious intent) produce a display of the outer surface or silhouette of the whole body or a body part such as torso or head. Due to the penetrating properties of e.g. X-rays and MR signals, the patient then appears "naked" in the rendering, and may even be recognizable visually. Some patients may perceive this sort of rendering of their head or torso as inappropriate if seen by unauthorized or non-medical personnel, or even when seen inadvertently by medical personnel when there is no medical necessity for this. Abuse may be ripe for instance by publishing this volume renderings through communication networks (internet postings, social media) if the data falls into unauthorized hands, for instance if the mobile storage device on which the data is held gets lost or is stolen or is otherwise procured illegally by hacking the user's computer, etc.

The wide-spread availability of this kind of rendering software may discourage patients from giving their consent for medical imaging or from making their image data available for clinical studies.

SUMMARY OF THE INVENTION

There may therefore exist a need for methods or apparatuses to address the above identified data protection concerns and similar issues. The object of the present invention is solved by the subject matter of the independent claims where further embodiments are incorporated in the dependent claims. It should be noted that the following described aspect of the invention equally apply to the image processing apparatuses, to the computer program elements and to the computer readable media.

According to a first aspect of the invention there is provided an image processing method, comprising:

receiving a three-dimensional, 3D, image data set acquired of an object;

segmenting the image data set into an object region and, complementary thereto, a background region; and applying a randomizing operation to image elements in the background region to thereby transform the 3D image data set into an at least partly randomized image data set.

In other words, a (digital) segmentation algorithm is employed to automatically identify the airspace around the body or body parts in the 3D image volume. The identified outer air volume may then be superposed with intensities from a random number generator. Any subsequent direct volume rendering or other manipulation would only yield an unspecific display of the body surface whilst retaining full resolution inside the body to ensure the transformed data set can still be used of medical diagnosis for instance. As proposed herein, randomizing is not merely blurring by changing resolution but in here the original mage information is combined with by random image intensities to render the body contour unrecognizable.

According to one embodiment, the object region comprises an inner core region and an outer layer region, the outer layer region being situated between said inner core region and said background region, wherein the randomizing operation is confined to i) image elements in said background region and ii) image elements in said outer layer region.

In other words, randomization may extend down to a certain "skin depth" (one or more but in general merely a few voxels, 1-5 or instance) into the body region to achieve better anonymization.

According to one embodiment, the outer layer region includes the image elements that interface (IF) said background region. In other words, the randomization extends only one voxel deep into the object region.

According to one embodiment, the outer layer region comprises only said interfacing image elements. This avoids saving computation time.

According to one embodiment, the randomization operation comprises combining original image information at a given image element with randomized image information. This allows later recovering the original image data if need be.

According to one embodiment, a preponderance (or amount) of the randomized image information over the original image information increases for image elements along a direction from the outer layer region towards the background region. This avoids hard transitions between randomized and non-randomized image regions. Better anonymization can be achieved.

According to one embodiment, the randomizing operation is reversible to afford substantially restoring the original image data set.

According to one embodiment, the reversal of the randomization operation is defined by one or more randomization reversal instructions that are stored in association with the randomized image data set.

According to one embodiment, the one or more randomization reversal instructions are stored at least in parts in a DICOM header date of the randomized image data set.

According to one embodiment, the one or more randomization reversal instructions are stored separate from and away from the randomized image data set.

According to one embodiment, the randomization reversal instructions are executable only by an authorized agent, for instance by querying a password or by having the appropriate user rights conferred in a multi-user operating system (such as UNIX).

In sum, it is proposed herein to "fill" of the imaged airspace surrounding the imaged body with "artificial noise" preferably before making the image data available so that any inadvertent volume rendering of the body surface becomes impossible, whilst at the same time, the image information about large parts of the internal organs of interest are retained at full resolution. Preferably the randomization is applied automatically, that is, is applied after production of image data without a user specifically requesting same although embodiments for user requested randomizations are not excluded herein.

According to second aspect, there is provided a further image processing method, comprising:

receiving an at least party randomized three-dimensional, 3D, image data set acquired of an object;

accessing randomization instructions;

forming reversed randomizing instructions based on said randomization instructions;

applying said reversed randomizing instructions to transform the randomized 3D image data set to a non-randomized 3D image data set.

This method according to the second aspect allows essentially reversing the randomization operation as per the method according to the first aspect to recover the original image data set.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
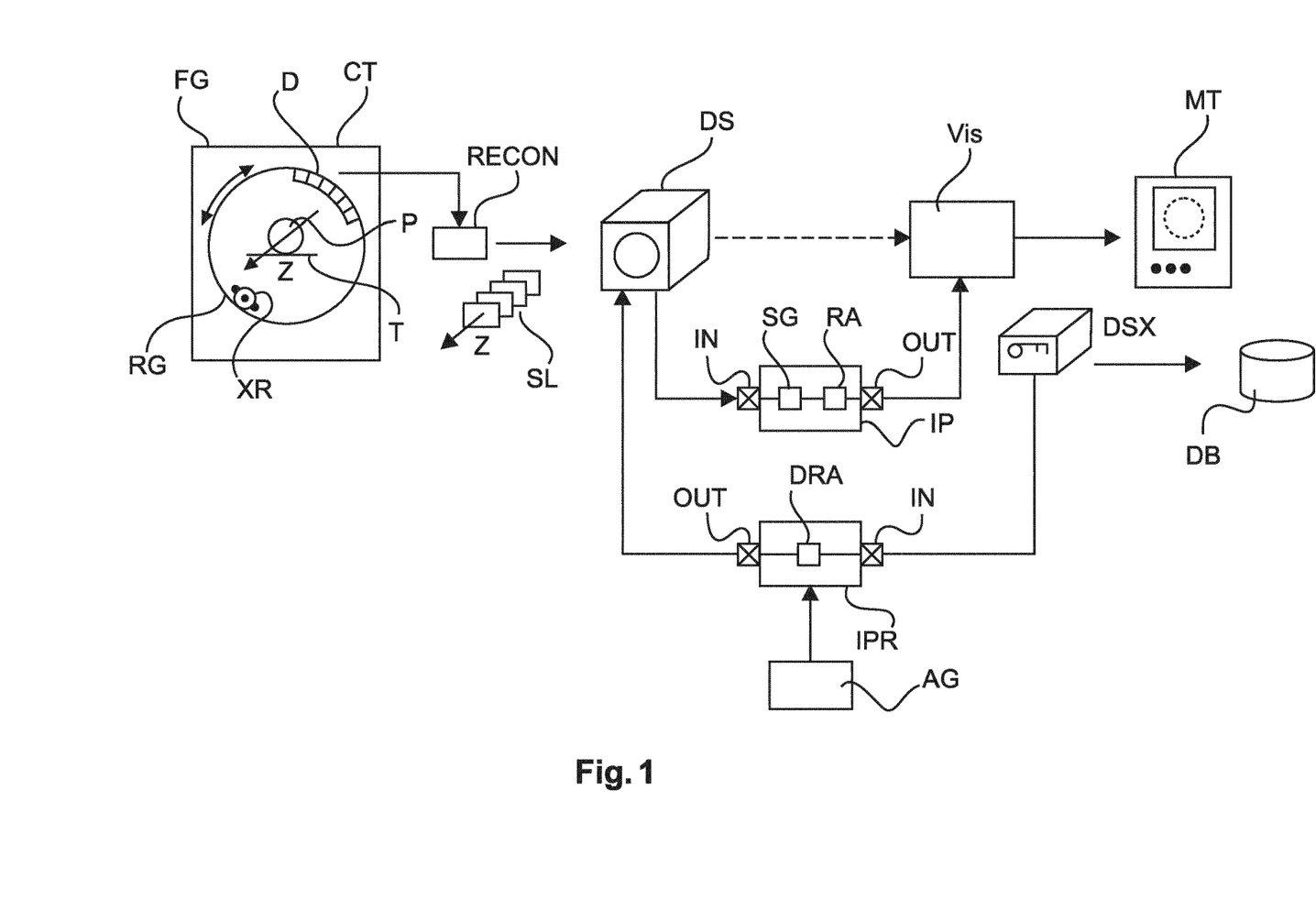
FIG. 1 shows a schematic block diagram of an imaging arrangement.

With reference to FIG. 1, there is shown a schematic block diagram of an x-ray imaging system CT such as computed tomography scanner. In one embodiment, the imaging system CT (also referred to as "scanner" or "imager" herein) includes a rotatable gantry RG rotatably mounted in a fixed gantry FG. The rotatable gantry RG is rotatable about a portion of space, an examination region that is. More specifically rotatable gantry RG is rotatable around an iso-center of said examination region. The rotatable gantry RG carries at one of its ends an x-ray tube or source XR and on the other end a detector D.

The x-ray source XR is configured to emit, during an imaging session, x-ray radiation. More particularly, an X-ray beam passes through the examination region and then impinges on a radiation sensitive surface of the detector D. Within the examination region traversed by the x-ray beam is an examination table T. On the examination table T, a sample/object P to be imaged (for instance, a human or animal patient) is deposited. Yet more particularly, the x-ray beam passes through patient P at a region of interest ROI, e.g. a specific organ or part thereof, such as the patient's chest. During its passage through the sample P, the x-ray beam is modified for instance by absorption interaction within matter in the sample P. The degree of absorption is a direct measure of the absorption co-efficient distribution or of the density distribution in the patient. Individual rays of the x-ray beam are therefore differently modified or absorbed depending on where the respective rays pass through the sample P. The so modified x-ray beam that emerges at the other end of the patient then interacts with the detector. Depending on the intensity detected at the detector, corresponding electrical signals are issued which are then passed to a DAS (data acquisition system—not shown). The DAS includes suitable A/D conversion circuitry to convert said electrical signals into digital form, also referred to as detector raw data, essentially an array of numbers.

The detector raw data produced by the imager CT essentially projection images of the imaged sample acquired at a certain projection direction relative to the examination region and the object therein.

As the rotatable gantry RG orbits around the examination region, and thus around the object P, a series of different projection images along different projection directions are acquired in the above described manner.

The series of projection images are the forwarded to a reconstructor RECON that uses otherwise known reconstruction algorithms (such as filtered back-projection FBP) to convert the series into a slice image SL that affords a cross-sectional view of the objet at a certain position z along an axis running through the object at the scanner's iso-center. A relative motion along said axis is then effected by moving the gantry or advancing the examination table T (on which the patient P resides) along said axis to a new z position and the above described procedure is repeated to form a new reconstructed slice for said new z position from new projection images. In this manner a plurality of slice images SL is formed that together define a 3D image data set. A visualization module VIS, such as direct volume renderer (DRV), may then be applied to the 3D image data set to form on screen MT desired 3D views on the anatomy from a view point interactively definable by the user.

Each image volume element ("voxel") of the 3D image data corresponds to a spatial point in the examination region. If that point was occupied by the object during the imaging then that point will carry the desired information about the amount of accumulated absorption suffered by a ray of the X-ray beam in its passage through said point in the examination region. But because the object P to be imaged does not normally fully occupy the whole of the examination region, there will inevitably be some background voxels that do not encode any attenuation caused by the object but will merely encode the negligible attenuation caused by the surrounding air. These voxels may then be called background voxels. In yet other words the whole of the volume set 3D comprises two complimentary regions: an object region OR and a background region BR. These are shown diagrammatically on pane A of FIG. 2.

Figure 2:
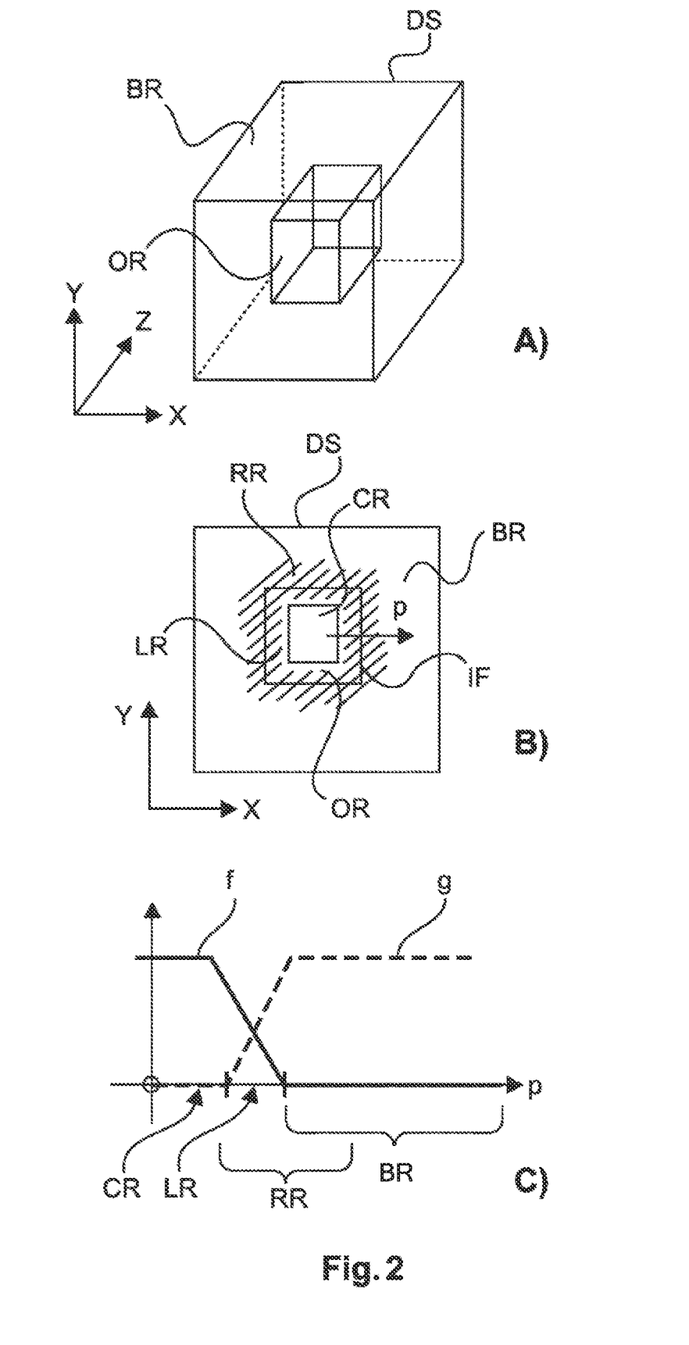
FIG. 2 shows a 3D image data set.

Pane B of FIG. 2 shows a cross section along Z direction through 3D data set DS. Where the two regions meet there is an interface IF. The interface region is essentially a two dimensional surface that corresponds or defines the outer contour or silhouette of the object P. Because of the high spatial resolution capabilities of modern imagers, the silhouette IF of the object may be represented in quite great detail in DVR viewers. On occasions the silhouette of the head for instance will allow identification of the imaged person. This may be undesirable because of privacy concerns. Although, for diagnostic purposes or other medical purposes, medical staff will mostly be interested in observing 3D renderings of the internals of the object, there is nothing that would prevent for instance an unauthorized person to request a volume rendering of the silhouette and then possibly abuse this potentially embarrassing imagery.

Figure 3:
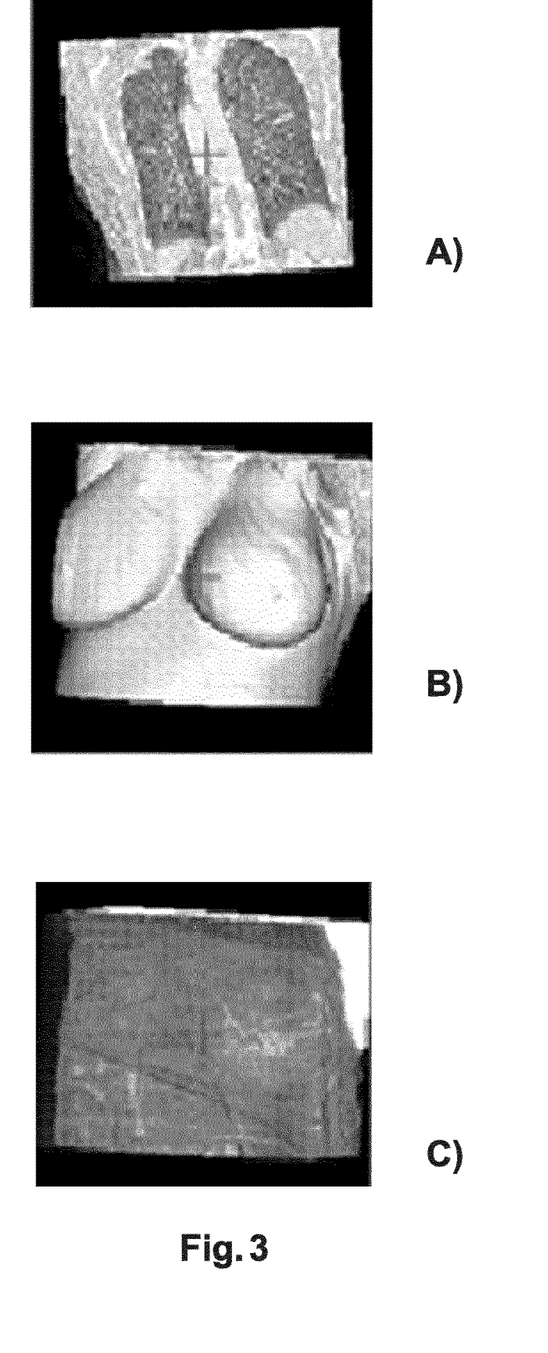
FIG. 3 shows volume renderings of a 3D data set.

This situation is illustrated in FIG. 3 by exemplary imagery in panes A,B. Pane A shows a direct volume rendering DVR of thoracic CT data set. In pane B, for the same data set, a viewpoint outside the object region is chosen and volumetric rendering of the torso silhouette is obtained. In other words, in the DVR of B the same settings are used as in pane A, but this time the view is turned around the cranial-caudal body axis thereby clearly revealing possibly embarrassing details about the outer contours or body surface of the patient.

Now, in order to protect the patient's privacy but at the same time conserve most of if not all image information about the internals of object P, an image processing module IP is proposed herein. Broadly speaking the proposed image processor IP operates to, according to one embodiment, automatically "fill up" the background region BR of the 3D data set DS with random pixel/voxel information so that any inadvertent volume rendering of the body contour is made next to impossible. In this manner the data set DS is transformed into a "visually protected" data set version DSX. In one embodiment this partial randomization of the data set DS is reversible so that the original, unprotected volume data set can be fully recovered. This includes storing randomization instructions which can be later used to "descramble" the randomized data set. The proposed image processor IP is envisaged as a security component interposed between the image output of imager CT and the visualization module (e.g. renderer) VIS. That is, rather than passing the produced 3D data set DS direct to the visualizer VIS as has been done in the past, now the image processor IP is interposed that first transforms the 3D data set DS into the visually protected one DSX. It is only the visually protected or randomized data set DSX that is then made unavailable for rendering operations.

FIG. 2B illustrates in more detail the operation of the image processor IP in terms of what happens to the various image voxels making up data set DS. The randomized region RR (that is, those voxels to which the randomization operation has been applied to or is to be applied to) includes all or parts of the background region BR. In fact, in certain embodiments the randomization region is restricted to the background region. However, in a preferred embodiment the randomization region RR extends partly into the object region. Conceptually, one can think of the object region OR to be made up of a core region CR that is surrounded by an outer layer region LR. This outer region LR may be merely a few voxels thick, in the extreme case merely one voxel thick. It is then envisaged in one embodiment to extend the randomization region RR into the object region to include the outer layer region LR. Preferably but not necessarily, all image elements in the outer layer region LR are randomized. Having the randomization extend into said outer layer region LR, affords a better anonymization outcome if, for instance, the randomization is applied only to the background region, there may be a tell-tale abrupt transition between background randomization and the non-randomized image information in the object region OR. The body contour may then still be recoverable. It is therefore desirable to at least randomize the interface IF along with at least part of the surrounding background region BR. That is, one randomizes not only the background region BR but also at least those object voxels in the object region OR that border the background region. In this manner the privacy of the patient can be protected better. The preferred embodiment is illustrated in FIG. 2B, where the randomization RR (shown as hatched) is partly extending from background region BR into outer layer region LR of object region OR.

In one embodiment it is envisaged that the amount of randomization increases in any or at least one direction p from the core region CR towards the background region BR. This is shown graphically the two curves in pane C of FIG. 2. Curves f, g show, respectively, the amount of original image information (f) and the amount of randomized image information (g). In the core region CR there is only original image information. However, when one moves along direction p into the outer layer region LR, the amount of original information f increases whereas the amount of "mocked" or randomized image information g and this reciprocity carries on up to the interface region IF. Once outside interface region IF in the background region BG, there is then only randomized pixel information and no more original image information. In one embodiment it is envisaged to randomize the whole of the background region. However, in a more refined embodiment one first constructs the convex hull of the object region OR. The randomization is then restricted to image elements in between the object region OR and the convex hull. Preferably but necessarily all, image elements between the convex hull and the object region OR are randomized. In this manner CPU can be saved. In other embodiments one may define a further layer region (not necessary the convex hull) of a fixed pre-selectable thickness around object region OR and randomizes only here.

Operation of image processor IP will now be explained in more detail.

Image processor IP includes input IN and output OUT ports for respectively receiving the original 3D data set DS and for outputting the randomized data set DSX.

The image processor includes as its basic components a segmenter SG and a randomizer RA. Reference is now made to FIG. 3C that shows the effect of the randomization operation on the data set shown in panes A, B of FIG. 3. In this example, the breasts of the patient are no longer visible. In other words, using the randomized data set DSX, if one requests a direct volume rendering of the internals of the patient one would still get the image as per FIG. 3A. However, when rendering from a view point outside the object region, one gets instead of the view in pane B the anonymized view as per pane C. In other words, the patient's body appears to be wrapped up to in a "virtual blanket" to better protect privacy.

Figure 4:
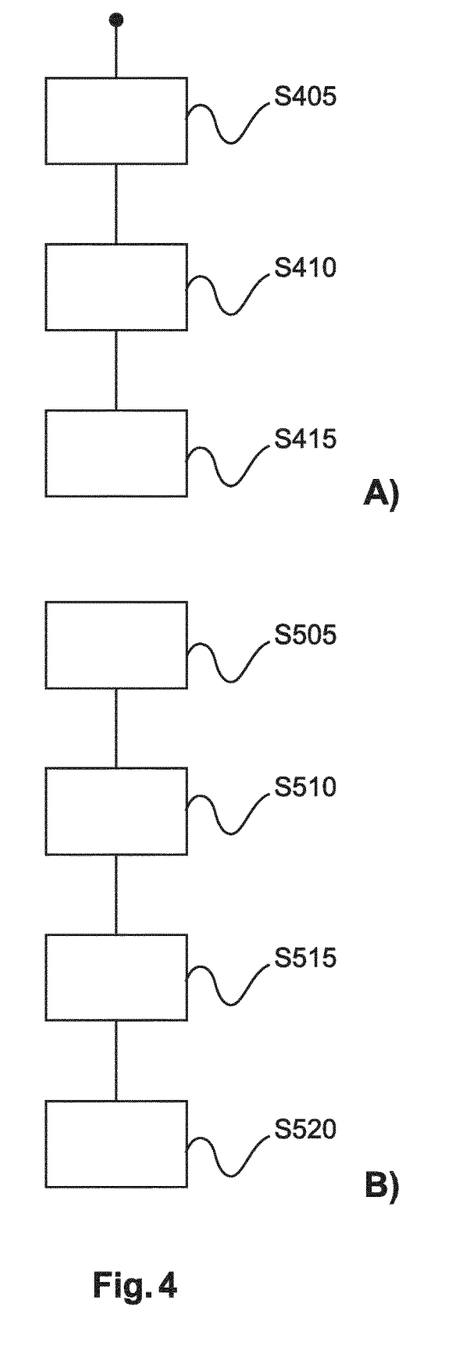
FIG. 4 shows flow charts of image processing methods.

Reference is now made to FIG. 4A showing a flow chart of steps S405-S415 that underlie the operation of image processor IP as proposed herein.

At step S405 the original 3D data set DS is received. As mentioned briefly above, this may occur automatically as a matter of course upon output of the volume by imager CT but other embodiments are also envisaged where the user can later effect the anonymization. For instance, the original set DS may be stored first in a database or storage DB and is then later anonymized. In fact, the proposed processor IP may be used to anonymize already existing stock of imagery held in a PACS or other image management system.

At step S410 the 3D data set is segmented into the body region OR and the background region BR. This allows defining the interface region IF that voxel elements that represent the 2D surface of the body. Also in this step, the identity of all the voxels to be randomized can be defined. That is the number and location (in terms of coordinates (x,y,z)) of the voxels (to be) randomized is completely determined once the thickness of the outer layer LR has been set and once it is defined how much of the background region is to be randomized. The latter can be set by defining the thickness of the layer region in the background BR around the object region OR as by computing the convex hull as previously explained. These two layers that define the "reach" of the randomized region RR into either side of the interface contour IF are pre-defined settings of the image processor IP and may be user adjustable. In yet other words, the voxels making up the region RR are those that are earmarked for the subsequent randomization.

At step 415 the randomization is then applied to the segmented data set, that is, is applied to the voxels in the randomized region RR. As per the extent of the RR, the randomization operation is either restricted to the background information or extends into the outer layer region as previously explained.

The actual randomization operation is implemented by using, in one embodiment, a pseudo random number generator. The random number generator is defined by a seed point, and a mathematical instruction that defines a sequence of numbers that are deterministic but appear as random if one is not in possession of the seed point and the particular functional description of the mathematical instructions. The mathematical instruction is in one embodiment an iterative modulo division (known from arithmetic) is carried out starting from the seed point (a number that is). In this process different remainders are generated that are output as the random numbers during the iteration. The collection of all the information that is necessary to generate this sequence of random numbers will be referred to herein as the randomization instruction(s).

Although not necessary in all embodiments, the randomization is operation is reversible. This can be achieved by defining a "traversal order" in which the random numbers generated in the sequence are to be applied to the randomized region RR. This can be done by defining a path through the region RR from slice to slice and in each slice row or column wise. Each voxel is then assigned an order number along said path. Because the overall number of voxels in region RR is known, an equal number of random numbers can then be generated by running the random generator for the required number of iterations to produce a sequence of random numbers having as many entries as the region RR has voxels. The i-th random number in the random sequence is then applied to the i-th voxel in the traversal path. Application of the random numbers to the region RR is by combining the two, or instance by adding the randomized intensity to the respective voxel value at the corresponding position to so form the randomized region. Each pixel in the randomization region is visited will then have the random intensity added.

The above randomization procedure admits to variety of different implementations all of which are envisaged herein in different embodiments. In one embodiment all random numbers are generated beforehand and are then applied to the randomization region. The application, that is the adding of the randomized intensities can proceed either sequentially or can be done in parallel at once. In another embodiment, the random intensity values are applied on-the-fly as they are output by the random number generator.

In general, before one can add the random numbers to the voxel values a meaningful conversion into image intensities may be required. In one embodiment, the generated random numbers are mapped to the admissible range of image intensities and then added in a linear superposition to respective ones of the voxels in the region RR. Alternatively, or additionally, the random numbers are "wrapped" around admissible range in an arithmetic modulo operation to arrive at the randomized intensity.

According to one embodiment the amount of randomization is on a "sliding scale" so varies within the randomization region. This could be implemented by filling the transition region LR up to the surface IF between air and body as per an increasing linear mixture of noise and true image intensities, such that the noise contribution is 100% at e.g. −5 mm before the body surface IF, until 0% at e.g. +5 mm inside the body. The percentage slides or is ramped down linearly as one moves toward the background region BR. That is, the true values are gradually phased and the mocked intensity values are phase in with decreasing distance.

The so randomized 3D data set DSX may then be stored for later reference in a database DB.

In one embodiment, the data DS is made available in the DICOM format. It is then proposed according to one embodiment that all or at least parts of the randomization instructions are included in the DICOM header of the data set DS. As mentioned earlier, in one embodiment, the randomization is executed upon production or generation of the data set at the imager CT. The inclusion of at least parts of the randomization instructions into the DICOM header can be implemented as a new standard for instance. However, in other embodiments the randomization instructions are stored elsewhere and are merely logically linked with the randomized data set DSX. For instance, the mathematical instruction of the pseudo random number generator, its seed number, and the body segmentation are stored together with the protected dataset as text in a DICOM file.

As mentioned, according to one embodiment there is also the option to reverse the randomization operation to allow recovery of the original data set DS. To this end, a reverse image processor IPR to the previously introduced image processor IP is envisaged.

The reverse image processor IPR includes in and out ports IN, OUT and includes a de-randomizer component DRA. It is understood that although FIG. 1 shows both operators IP and IPR, the latter is optional.

Operation of said reverse image processor IPR will now be explained in more detail with reference to flow chart B in FIG. 4.

At step S505 the randomized data set DSX is received.

At step S510 the randomization instructions are accessed. The request to access same can be issued by an agent AG. For instance, in a client-server-architecture, the agent AG may be the workstation of a physician in a medical PACS system. If the user at workstation AG has the right credentials, for instance passwords or has been given appropriate user rights, the request to access the randomization instructions is granted, otherwise denied.

If access is granted, the flow proceeds to step S515, where reversed randomization instructions are formulated. This may be achieved by re-running the randomization sequence using the same seed number and the same iterative mathematical instruction to recreate the random numbers.

In the follow up step S520 the reverse instructions are then applied to the randomized data set DSX at the designated voxel position as prescribed by the co-ordinates of the randomized region RR. Using the same traversal order, and the identity of the voxels in the randomized the randomized intensity can be subtracted from the randomized data set DSX at the respective positions to so reveal the original data set DS.

It should be clear from the above, that the randomization instructions include the previously mentioned seed point, the iterative mathematical function that generates the sequence of randomization points when iteratively applied to the seed points, the agreed on traversal order through the randomization region RR and a coordinate definition of the randomized region itself. The RR definition is based on the body segmentation at step S410 and can be stored as ASCII text (string data) together with the protected dataset (e.g. a DICOM file) or away from the protected date. The randomized region RR can be stored very memory-efficient e.g. as a mesh or as a compressed bit volume that requires typically <1% of storage compared to the original image data.

However, such items as the traversal order may be part of a pre-agreed standard so may not be specifically stored along with the other information. The items may be stored together or any one or more of the items may be stored away and separately from the others to increase security.

In one embodiment, it is for instance the seed number of the pseudo random number generator (a single integer number that is) is not stored together with the protected image, but for data security reasons is provided in a separate file and/or is provide in separate communication channels, which could be an electronic record, a paper printout, oral communication, telecommunication, etc.

As mentioned earlier, in one embodiment, recovery is allowed only for authorized personnel (e.g. the principal investigator or primary physician). This can be achieved on a password basis. For instance, in a non-limiting example (any other combination is also envisaged), the following items are stored with the image data: the randomization instruction for instance the mathematical formula of the pseudo random number generator, its seed, and the coordinate definition of the randomized region RR, The items may for instance stored be embedded, (in the DICOM header or otherwise). But the randomization instruction so stored is encrypted with a password.

In sum what is proposed herein is a technical possibility to automatically fill the body-surrounding space of the 3D data set with random noise before storage, so that any inadvertent volume rendering of the body surface becomes impossible, yielding a visually protected dataset. An additional option foresees that the addition of noise is reversible, so that a full recovery of the original unprotected volume data is possible by storing the appropriate information in a compact manner together with the protected dataset.

The image processors IP, IPR are envisaged as modules installed on scanner consoles or medical imaging and PACS workstations. In short, the proposed image processors may be used in any system which produce or handle 3D data sets. Processors PR and IPR may be consolidated into a single module, unlike the embodiment shown in FIG. 1, although having them separate as shown in FIG. 1 may also be desirable in some embodiments. For instance, IP is installed at on the scanner CT whereas descrambler IPR is made available only at select imager or PACS workstations.

Although the above embodiments have been explained for tomographic X-ray scanner the proposed methods and apparatuses IP, IPR are of equal application to MR imagery.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing method, comprising:
   receiving a three-dimensional (3D) image data set acquired of an object of a subject's body;
   segmenting the 3D image data set into an object region that is internal to the subject's body and, complementary thereto, a background region that is external to the subject's body;
   identifying an interface between the object region and the background region;
   applying a randomizing operation to image elements in the background region adjacent the interface and including the interface to thereby transform the 3D image data set into a partly randomized image data set; and
   storing the partly randomized image data set to enable subsequent communication to a visualizer in lieu of the 3D image date set, thereby preventing a clear visualization of the interface at the visualizer.

2. The image processing method of claim 1, wherein the object region comprises an inner core region and an outer layer region, the outer layer region being situated between the inner core region and the interface, wherein the randomizing operation is confined to image elements in the background region and image elements in the outer layer region.

3. The image processing method of claim 2, wherein the randomization operation is confined to the image elements in the background region.

4. The image processing method of claim 2, wherein the outer layer region has a thickness of between one and five voxels.

5. The image processing method of claim 1, wherein the randomization operation comprises combining original image information at a given image element with randomized image information.

6. The image processing method of claim 5, wherein a magnitude of the randomized image information over the original image information increases for image elements along a direction from the outer layer region towards the background region.

7. The image processing method of claim 1, wherein the randomizing operation is reversible to enable substantially restoring the original image data set.

8. The image processing method of claim 7, wherein the reversal of the randomization operation is defined by one or more randomization reversal instructions that are stored in association with the partly randomized image data set.

9. The image processing method of claim 8, wherein the one or more randomization reversal instructions are stored in a Digital Imaging and Communications in Medicine (DICOM) header data of the partly randomized image data set.

10. The image processing method of claim 8, wherein the one or more randomization reversal instructions are stored separate from and away from the partly randomized image data set.

11. The image processing method of claim 7, wherein method includes receiving information to determine whether an agent is authorized to reverse the randomization and enabling the reversal only by an authorized agent.

12. A non-transitory computer readable medium that includes a program that, when executed by a processing unit, causes the processing unit to perform the method of claim 1.

13. An image processing method, comprising:
    receiving a partly randomized three-dimensional (3D) image data set acquired of an object of a subject's body, wherein the partly randomized 3D image data set obscures an interface between an object region internal to the subject's body and a complementary background region external to the subject's body;
    accessing randomization instructions;
    forming reversed randomizing instructions based on the randomization instructions;
    applying the reversed randomizing instructions to transform the partly randomized 3D image data set to a non-randomized 3D image data set; and
    outputting the non-randomized 3D image data set to a visualizer in lieu of the partly randomized 3D image data set, thereby enabling a clear visualization of the interface at the visualizer.

14. A non-transitory computer readable medium that includes a program that, when executed by a processing unit, causes the processing unit to perform the method of claim 13.

15. An image processing apparatus, comprising:
    an input port configured to receive a three-dimensional (3D) image data set acquired of an object of an subject's body;
    a segmenter configured to segment the 3D image data set into an object region internal to the subject's body and, complementary thereto, a background region external to the subject's body, and to identify an interface between the object region and the background region;
    a randomizer configured to apply a randomizing operation to image elements in the background region adjacent the interface and including the interface to thereby transform the 3D image data set into a partly randomized image data set; and
    an output port configured to output the partly randomizer image data set to enable communication of the partly randomized image data set to a visualizer in lieu of the 3D image data set, thereby preventing a clear visualization of the interface at the visualizer.

16. The image processing apparatus of claim 15, wherein the object region comprises an inner core region and an outer layer region, the outer layer region being situated between the inner core region and the interface, wherein the randomizing operation is confined to image elements in the background region and image elements in the outer layer region.

17. The image processing apparatus of claim 15, wherein the randomization operation comprises combining original image information at a given image element with randomized image information.

18. The image processing apparatus of claim 17, wherein a magnitude of the randomized image information over the original image information increases for image elements along a direction from the outer layer region towards the background region.

19. The image processing apparatus of claim 15, wherein the randomizing operation is reversible to enable substantially restoring the original image data set, and is defined by one or more randomization reversal instructions that are stored in association with the partly randomized image data set.

20. An image processing apparatus, comprising:
    an input port configured to receive a partly randomized three-dimensional (3D) image data set acquired of an object of a subject's body; wherein the partly randomized 3D image data set obscures an interface between an object region internal to the subject's body and a complementary background region external to the subject's body;
    a de-randomizer configured to access randomization instructions and to form therefrom reversed randomizing instructions and configured to apply the reversed randomizing instructions to transform the partly randomized 3D image data set into a non-randomized 3D image data set; and an output port configured to output the non-randomized 3D image data set to enable communication of the non-randomized 3D image data set to a visualizer in lieu of the partly randomized 3D image data set, thereby enabling a clear visualization of the interface at the visualizer.

* * * * *